US008481280B1

(12) United States Patent
Haas

(10) Patent No.: US 8,481,280 B1
(45) Date of Patent: Jul. 9, 2013

(54) METHOD FOR DETERMINING ACTIVITY OF AN ANTIBIOTIC WITH HOPS

(75) Inventor: Gerhard J. Haas, Woodcliff Lake, NJ (US)

(73) Assignee: S. S. Steiner, Inc., New York, NY (US)

( * ) Notice: Subject to any disclaimer, the term of this patent is extended or adjusted under 35 U.S.C. 154(b) by 622 days.

(21) Appl. No.: 11/585,699

(22) Filed: Oct. 25, 2006

Related U.S. Application Data

(63) Continuation-in-part of application No. 11/434,660, filed on May 17, 2006, now Pat. No. 8,367,086, which is a continuation-in-part of application No. 10/991,221, filed on Nov. 18, 2004, now Pat. No. 7,641,923, which is a continuation-in-part of application No. 10/769,654, filed on Feb. 2, 2004, now Pat. No. 7,364,747.

(51) Int. Cl.
*C12Q 1/18* (2006.01)

(52) U.S. Cl.
USPC .......................................................... 435/32

(58) Field of Classification Search
USPC ........................................... 435/32, 29
See application file for complete search history.

(56) References Cited

U.S. PATENT DOCUMENTS

| 5,563,043 | A | * | 10/1996 | Schalkowsky et al. | 435/32 |
| 6,043,048 | A | * | 3/2000 | Johnston et al. | 435/32 |
| 6,472,166 | B1 | * | 10/2002 | Wardlaw et al. | 435/32 |
| 7,361,374 | B2 | * | 4/2008 | Wilson et al. | 424/778 |
| 7,364,747 | B1 | * | 4/2008 | Haas | 424/405 |
| 2001/0039032 | A1 | * | 11/2001 | Matsumura et al. | 435/32 |

OTHER PUBLICATIONS

Haas G. et al. Critical Role of Amino Acids on the Sensitivity and Development of Resistance to Polymyxin B. Archives of Biochemistry and Biophysics 43(1)11-24, Mar. 1953.*
Natarajan P. et al. Positive Antibacterial Co-Action Between Hop Constituents and Selected Antibiotics. Phytomedicine 15(2008)194-201.*
Junior A. et al. Propolis: Anti-*Staphylococcus aureus* Activity and Synergism with Antimicrobial Drugs. Memorias do Instituto Oswald Cruz 100(5)1-7, Aug. 2005.*

* cited by examiner

*Primary Examiner* — Ralph Gitomer
(74) *Attorney, Agent, or Firm* — Walter D. Ames

(57) ABSTRACT

A method for determining the combined activity of two or more ingredients by impregnating a carrier with one ingredient and bringing it into contact with target material to create a zone of inhibition, then adding a second ingredient to the target material and bringing the carrier into contact with it to create a second zone of inhibition. The zones are then compared.

5 Claims, No Drawings

METHOD FOR DETERMINING ACTIVITY OF AN ANTIBIOTIC WITH HOPS

This application is a CIP of Ser. No. 11/434,660 filed May 17, 2006, now U.S. Pat. No. 8,367,086, which is a CIP of Ser. No. 10/991,221 filed Nov. 18, 2004, now U.S. Pat. No. 7,641,923, which is a CIP of Ser. No. 10/769,654 filed Feb. 2, 2004, now U.S. Pat. No. 7,364,747.

FIELD OF THE INVENTION

The present invention relates generally to the ascertainment of the activity of certain materials. More specifically it relates to the determination whether two materials have a combined activity and, if so, the extent of that combined activity.

BACKGROUND OF THE INVENTION

An important precursor of my novel method is the disc diffusion test that is known in the microbiological art as the Kirby-Bauer test. In this method a filter paper disc impregnated with a chemical is placed on agar so that, with or without incubation, the chemical in the disc will diffuse from the disc into the agar. If a susceptible organism is placed in or on the agar, it will not grow in the area surrounding the disc if the organism is susceptible to the chemical, and this lack of growth is visually apparent. The area around the disc created by the lack of growth is known as the zone of inhibition.

The Kirby-Bauer method has been used to test the effectiveness of a variety of antibiotics against various pathogens. Many factors are considered in testing effectiveness, e.g., the agar utilized, the depth of the agar, the quantity of organisms in the agar, and the conditions of incubation, which are maintained as a constant. Under these conditions, the zone of inhibition will be the only variable, and the greater the zone, the more effective will be the antibiotic. The size of the zone of a particular antimicrobial may also be influenced by the diffusion capability of the substance.

While the Kirby-Bauer disc diffusion test has, to the best of my knowledge, previously found primary use in the determination of antimicrobial properties of various materials, it can also be more broadly used. Thus, while the indicator that is dispersed in the agar or another gel is usually a bacterium, the indicator can be other living organisms such as yeast, plantlets, seeds, algae, or chemicals that cause an opalescence in the gel, such as an oil, fat, cellulose, starch, etc. When the material that has been impregnated into the disc is applied to the gel or agar, a halo of change in the gel will indicate a zone of activity of the impregnated material. With specific respect to a determination of antibiotic activity, after incubation a clear halo about the disc will indicate the extent of activity of the antibiotic impregnated in the disc.

SUMMARY OF THE INVENTION

In its most general terms, my invention comprises an advancement of the standard disc diffusion method to determine whether there is a combined activity gained when two or more active compositions are utilized together for a specific purpose. In my method, target material is provided, as in Kirby-Bauer, as a suspension, gel, solution or other suitable medium. Also provided is a carrier that is impregnated with a first substance. The target material may, for example, be bacteria. The impregnated carrier is brought into contact with the target material to create a zone of activity, which is then measured.

My invention differs from the Kirby-Bauer method because thereafter, utilizing the same parameters as the initial test, one then disperses a second active composition in the target material to create a modified target material. The same impregnated carrier is then brought into contact with the modified target material to create a second zone of activity extending from the carrier into the modified target material, and the first and second zones of activity are compared. When the second zone of activity is greater than the first zone, that is indicative that there is a co-action between the first and second active compositions with respect to the target material. If the zones are the same, that is indicative of a lack of co-action; a diminution in the size of the two zones indicates that the active materials are antagonistic to each other in their effectiveness against the target material.

Within that broad framework, many features are possible. Thus, it is a preferred embodiment of my invention that the target material is bacteria and that the first and second active compositions are antibacterial agents. Further, the carrier is conveniently a disc of filter paper and the target material, the bacteria, is dispersed in a gel or agar. Other variations of the invention are that the target material is a fungus and the active compositions or substances are fungicides. Alternatively, the target material may be a substrate material and the active compositions are enzymes being studied for reactivity with the substrate. Further, the target material may be seeds and the active compositions being studied are emergence inhibitors. Other uses of the method invention set forth herein is to judge the effectiveness of pesticides against the hatching of insect eggs; the effectiveness of a plurality of differentiation stimulators in encouraging differentiation of plantlets in tissue culture, and the co-action of germination enhancers where the target materials are bacterial spores. Most preferable at present is the ability of hop compounds to enhance the antibacterial activity of antibiotics.

It is, therefore, a primary object of the present invention to provide a simple method for determining the co-action, or lack thereof, of a plurality of active agents against a target material.

These and other objects, features and advantages of my invention will become more apparent when viewed in connection with preferred embodiments of the invention, which are set forth in the following detailed descriptions thereof.

DETAILED DESCRIPTION OF PREFERRED EMBODIMENTS

The method of my invention was used to determine the co-action, or lack thereof, of a combination of a hop composition and a known antibiotic to ascertain whether the addition of the hop composition resulted in greater activity than that of the antibiotic, alone. Various hop constituents, including the α and β resins (humulone and lupulone), as well as xanthohumol, were obtained from S. S. Steiner, Inc., of New York, N.Y. Polymyxin B and other antibiotics impregnated on discs were obtained from other commercial sources. In order to test the possible synergistic effect of mixtures of hop compositions and these antibiotics, the method of my invention was employed. It should be pointed out that in testing the effectiveness of various antibiotic-hops composites, all factors, such as the agar utilized, the depth of the agar, the amount of organisms used, and incubation conditions, were maintained constant for the various organisms and antibiotics being subjected to my method. Under these conditions the zone of inhibition was the only variable, and the greater the zone, the more effective were the active ingredients, either alone or in combination.

Example I

The purpose of this practice of my method was to determine the co-action of hop compositions and certain antibiotics. A bacterial suspension having an inoculum density of approximately $1 \times 10^8$ CFU/ml (colony forming units) was added to 10 ml of trypticase soy agar at 46° C. It was mixed thoroughly by vortexing and then poured into a plastic Petri dish. After hardening of the agar, filter paper discs ($\phi$7 mm) made from Whatman filter paper No. 1 that had been impregnated by the manufacturer, Becton Dickinson, Inc., with the suitable antibiotic, were placed on the agar. In this series of tests the ability of each antibiotic per se to control the growth of the bacteria was measured.

Another series of agar containing Petri dishes was then prepared using the same bacteria and density thereof as had been prepared for the prior test series. However, here hop compounds were also present in the agar. The hop compound, either lupulone, humulone or xanthohumol, was dissolved in ethanol. While certain of the hop components are only slightly soluble in water, they are very soluble in ethanol. An ethanol control was prepared in the same way. The various hop fraction solutions were diluted in such a way that when added to the media solutions, the 10 ml. of agar poured into the Petri dish would contain in addition to the hop compound, exactly 1% of ethanol, which in a control was found to be non-inhibitory to the bacteria.

In each test, after an incubation period of 24 hours, a homogeneous lawn of bacteria developed throughout the plate, and a clear zone of inhibition was evident around discs that contained inhibitory material. The size of the inhibition zones was measured to the nearest mm. The test results are demonstrated in the Table below. The Table evidences the results of disc diffusion assays where the bacterium was *Staphylococcus saprophyticus*, a gram positive bacterium. As will be evident from the results of the Table, in Experiment 1, the control, which was the antibiotic per se, had no effect whatsoever on the bacterium, that is, there was no inhibition zone whatsoever around the disc of filter paper when polymyxin B was used alone. However, when the same polymyxin B was used in conjunction with 0.2 µg/ml of β-resin, the result was a zone of inhibition of 9 mm. The non-obviousness of the increase in the zone of inhibition when a combination of polymyxin and hops are used is made evident by the same test when performed using the same hop compound in conjunction with other antibiotics. There the results were uniformly negative, i.e., there was no significant increase in the zone of inhibition when the resin lupulone was added in the same concentration in which it was added to the polymyxin composition. As the results of Table 1 show, neomycin per se had a zone of inhibition of 23 mm. When the lupulone was added to the agar, the zone increased to 25 mm. When the hop compound was added to streptomycin and erythromycin, the zones of inhibition remained constant, as they did with bacitracin. With penicillin, chloramphenicol and tetracycline, there was a decline in the zones.

The experiment was performed again in Experiment 2 and the results are tabulated in the Table. It will there be seen that with all of the antibiotics other than polymyxin B, there was no significant change in the radius of the zone of inhibition when the β-resin was present. However, when the hop compound was added to the polymyxin B compound, the increase in the zone was dramatic: from zero to 8 mm. Similar, synergistic results have been obtained with hop compounds and the antibiotics ciprofloxacin and tobramycin.

TABLE

| | Microorganism Tested: *STAPHLOCOCCUS SAPROPHYTICUS* | | | |
|---|---|---|---|---|
| | Experiment 1 | | Experiment 2 | |
| ANTIBIOTIC | Control | 0.2 µg/ml β-resin | Control | 0.2 µg/ml β-resin |
| POLYMYXIN | 0 | 9 | 0 | 8 |
| NEOMYCIN | 23 | 25 | 26 | 24 |
| STREPTOMYCIN | 15 | 15 | 15 | 14 |
| ERYTHROMYCIN | 23 | 25 | 23 | 23 |
| PENICILLIN | 41 | 39 | 37 | 35 |
| BACITRACIN | 0 | 0 | 0 | 0 |
| CHLORAMPHENICOL | 29 | 27 | 25 | 25 |
| TETRACYCLINE | 25 | 15 | 14 | 14 |

Example II

This example shows that the method evidences enhancement of the inhibitory activity of an antibiotic by the addition of xanthohumol. 10 ml of trypticase soy agar (TSA) was inoculated with the bacterium *Streptococcus salivarius*. This was accomplished by melting 10 ml of TSA in a boiling water bath, then cooling the liquid agar to 46° C., inoculating the microorganism and pouring the agar into a Petri dish to solidification. After hardening of the agar, the dish was incubated at 37° C. for 24 hours, whereupon a lawn of microbes appeared. This was designated as plate 1, a positive control for microbial growth.

Plate 2 assures that the microbes can grow in the presence of 3 µg of xanthohumol. A plate was prepared in a manner similar to plate 1 except that it contained 3 µg of xanthohumol/ml made by adding 0.1 ml of alcoholic stock solution of xanthohumol containing 300 µg/ml to 10 ml of the agar. Again there a lawn equivalent to that of plate 1 formed after 24 hrs. of incubation, evidencing that the bacteria could grow in this medium.

Plate 3 was then prepared. It was identical to plate 1 except that a disc containing 5 µg of ciprofloxacin was placed on the plate. After a 24-hour period of incubation, a zone of inhibition of bacterial growth had developed which measured 8 mm from the edge of the disc to the edge of the zone. Then plate 4, which was identical to plate 2, was prepared and a disc with 5 µg of ciprofloxacin was placed on the agar. This time the zone of inhibition measured 20 mm, showing considerable enhancement of antibacterial properties due to the presence of the xanthohumol in the agar.

Example III

The purpose of this example is to show how the method according to the present invention may be used to test for a possible co-action between cellulases. A water-insoluble cellulose or cellulose derivative such as carboxymethylcellulose or cellulose powder is suspended in an agar gel and a cellulase such as that derived from *Trichoderma viride* is placed on the paper disc at such a concentration that a small zone of activity shown by a clear zone forms around the disc upon incubation, evidencing the solubilizing of the cellulose or CMC. Then a second cellulase, for example, that derived from a strain of *Aspergillus niger*, is dissolved in the agar at a concentration such that it, alone does not attack the cellulose or CMC. The second cellulase is dissolved in the agar at a temperature that insures that it does so without loss of cellulose activity. If there is an enhancement of the size of the clear zone around the disc, that constitutes a showing that there has been a positive co-action. The same experiment can be carried out with amylases and lipases using a different indicator materials, such as starch for amylases and an emulsion containing olive oil or other fat for lipases.

Example IV

An example to show co-action of materials to suppress sprouting can be carried out according to my method. Here seeds would be spread on the surface of the agar and one sprouting inhibitor located in a well cut in the agar, the other dissolved in the agar. Such sprouting inhibitors are especially useful to make certain that vegetable tubers such as potatoes do not sprout in the vegetable bin of the consumer.

Example V

The present method has application as a germination enhancer for bacterial spores. One of the enhancers is dissolved in the agar, the other impregnated into a paper disc. A suspension of a spore former from the genus Clostridium is the indicator organism. After preparation of a seeded lawn, the Petri dish is anaerobically incubated at 37° C. for 10 hours. It is then heated at 60° C. for one hour to kill the vegetative bacteria. It is then reincubated for 24 hours at 37° C. and the number of colonies is counted. For this experiment 3% agar should be in the medium to be sure that it stays solid during the heating to 60° C. The number of colonies emerging after the second incubation should give a count of the cells not germinating during the first 10 hours.

Example VI

My method can also be used to determine possible co-action of differentiation enhancers for plant tissue cultures. A plantlet suspension culture is spread over a Murashige-Skoog agar and a plant hormone such as indole butyric acid is placed in subactive concentration on the agar. A second differentiation enhancer is placed on a disc or in a well. Any differentiation is then observed, and if the zone of increased differentiation around the disc or well is enlarged, co-action can be measured quantitatively and optimal conditions established.

It will be apparent to those of skill in this art that the invention previously described by way of specific examples will have application to other measurements of the co-action between differing materials directed to a specific purpose. As to all such other applications, it is desired that they be included within the purview of my invention, which is to be limited only by the scope, including equivalents, of the following, appended claims.

I claim:

1. A method for determining a presence or absence of combined antibiotic activity of a first antibiotic and a hops composition against a target microorganism, comprising:

providing the target microorganism in a carrier, said carrier being in the form of a solution, suspension or gel, contacting said target microorganism carrier with a discrete quantity of said first antibiotic for a period of time sufficient to create at the area of contact, a first zone of sensitivity of said target microorganism carrier sensitive to said first antibiotic, observing said first zone of sensitivity, dispersing a hops composition in said target microorganism carrier in an amount in which said microorganism will not exhibit sensitivity to create a hops-modified target microorganism carrier, contacting said hops-modified target microorganism carrier with said discrete quantity of said first antibiotic for a period of time sufficient to create at said area of contact, a second zone of sensitivity of said hops-modified target microorganism carrier sensitive to said first antibiotic, observing said second zone of sensitivity and comparing said first and second zones of sensitivity to determine whether said second zone is larger than said first zone and, therefore, whether the combined antibiotic activity of said first antibiotic and said hops composition against said target microorganism is greater than the antibiotic activity of said first antibiotic alone.

2. A method as claimed in claim 1, in which said target microorganism is provided in the form of a carrier gel.

3. A method as claimed in claim 2, in which said gel is agar.

4. A method as claimed in claim 1, in which said discrete quantity of said first antibiotic is impregnated on paper.

5. A method for determining the presence or absence of combined antibiotic activity of a first antibiotic and a hops composition against a target microorganism, comprising:

providing the target microorganism in the form of a carrier gel, contacting said target microorganism carrier gel with a discrete quantity of said first antibiotic impregnated onto paper for a period of time sufficient to create at the area of contact between the impregnated paper and the microorganism carrier gel, a first zone of sensitivity of said target microorganism sensitive to said first antibiotic, said first zone of sensitivity extending outwardly from said paper, observing said first zone of sensitivity, dispersing a hops composition in said target microorganism gel in an amount in which said microorganism will not exhibit sensitivity, to create a hops-modified target microorganism carrier gel, contacting said hops-modified target microorganism carrier gel with said discrete quantity of said first antibiotic impregnated onto paper for a period of time sufficient to create at the area of contact, a second zone of sensitivity of said hops-modified target microorganism carrier gel sensitive to said first antibiotic, said second zone extending outwardly from said paper, observing said second zone of sensitivity and comparing said first and second zones of sensitivity to determine whether said second zone is larger than said first zone and, therefore, whether the combined antibiotic activity of said first antibiotic and said hops composition against said target microorganism is greater than the antibiotic activity of said first antibiotic alone.

* * * * *